US006438533B1

(12) United States Patent
Spackman et al.

(10) Patent No.: US 6,438,533 B1
(45) Date of Patent: Aug. 20, 2002

(54) SYSTEM FOR RETRIEVAL OF INFORMATION FROM DATA STRUCTURE OF MEDICAL RECORDS

(75) Inventors: Kent A. Spackman, Tualatin, OR (US); Keith E. Campbell, Sunnyvale, CA (US)

(73) Assignee: College of American Pathologists, Northfield, IL (US)

( * ) Notice: Subject to any disclaimer, the term of this patent is extended or adjusted under 35 U.S.C. 154(b) by 0 days.

(21) Appl. No.: 09/431,291

(22) Filed: Oct. 29, 1999

Related U.S. Application Data

(60) Provisional application No. 60/106,465, filed on Oct. 30, 1998.

(51) Int. Cl.$^7$ .......................... G06F 17/00; G06F 17/60; A61B 5/00
(52) U.S. Cl. .......................... 706/45; 706/46; 600/300; 705/3
(58) Field of Search ..................... 706/45, 46; 600/300; 705/3

(56) References Cited

U.S. PATENT DOCUMENTS

| | | | | |
|---|---|---|---|---|
| 4,930,071 | A | 5/1990 | Tou et al. | 707/4 |
| 5,247,666 | A | 9/1993 | Buckwold | 707/100 |
| 5,577,241 | A | 11/1996 | Spencer | 707/5 |
| 5,659,724 | A | 8/1997 | Borgida et al. | 707/3 |
| 5,724,575 | A | 3/1998 | Hoover et al. | 707/10 |
| 5,903,889 | A | 5/1999 | de la Huerga et al. | 707/3 |
| 5,911,132 | A | 6/1999 | Sloane | 705/3 |

OTHER PUBLICATIONS

Spackman, Kent; Campbell, Keith; and Cote, Roger; "SNOMED RT: A Reference Terminology for Health Care"; 1997 AMIA Fall Symposium Proceedings; Journal of the American Medical Informatics Association Symposium Supplement; pp. 640–644.

Chute, Christopher; Cohn, Simon; Campbell, Keith; Oliver, Diane; and Campbell, James; "The Content Coverage of Clinical Classifications"; Journal of the American Medical Informatics Association, May/Jun. 1996.

Arens, Yigal; Knoblock, Craig; and Shen, Wei–Min; "Query Reformulation for Dynamic Information Integration";Jun. 15, 1995.

Arens, Yigal and Knoblock, Craig; "Planning and Reformulating Queries for Semantically–Modeled Multidatabase Systems"; Proceedings of the First International Conference on Information and Knowledge Management, Baltimore, MD, 1992.

Arens, Yigal; Hsu, Chun–Nan and Knoblock, Craig; "Query Processing in the SIMS Information Mediator"; 1994.

Rector, A.; Bechhofer, S.; Goble, C.; Horrocks, I.; Nowlan, W.; and Solomon, W.; "The GRAIL concept modelling language for medical terminology"; Artificial Intelligence in Medicine; 1997; pp. 139–171.

Rector, A.; Glowinski, A.; Nowlan, W.; and Rossi–Mori, A.; "Medical–concept Models and Medical Records: An Approach Based on GALEN and PEN&PAD"; Journal of the American Medical Informatics Association; 1995.

*Primary Examiner*—George B. Davis
(74) *Attorney, Agent, or Firm*—Sidley Austin Brown & Wood; Hugh A. Abrams (57) ABSTRACT

An apparatus and system are provided for retrieving electronic records from a database of records, preferably in the form of medical records. The apparatus utilizes a knowledge base in the form of a data structure set forth in a description language. The knowledge base includes representations of a plurality of concepts hierarchically linked with other concepts within a plurality of classes, and non-hierarchically linked with concepts in other classes. A query manager receives a user query and translates the query into the description language. A records analyzer is coupled to the query manager, database and knowledge base. The records analyzer analyzes the records in the database based on the user query and the classes and the hierarchical and non-hierarchical relationships in the knowledge base.

12 Claims, 6 Drawing Sheets

SNOMED INTERNATIONAL HIERARCHICAL CONSTRAINTS

FIG. 9

SYSTEM FOR RETRIEVAL OF INFORMATION FROM DATA STRUCTURE OF MEDICAL RECORDS

CROSS-REFERENCES TO RELATED APPLICATIONS

This application claims the benefit of U.S. Provisional Application No. 60/106,465, filed Oct. 30, 1998.

| Title | Application Ser. No. | Filing Date |
|---|---|---|
| Hypervideo: Information Retrieval Using Time-Related Multimedia | 09/430,437 | October 29, 1999 |
| Hypervideo: Information Retrieval Using Text from Multimedia | 09/430,597 | October 29, 1999 |
| Hypervideo: Information Retrieval Using Multimedia | 09/431,292 | October 29, 1999 |
| Hypervideo: Information Retrieval at User Request | 09/429,731 | October 29, 1999 |

BACKGROUND OF THE INVENTION

The present invention generally relates to the compilation, storage, transfer, retrieval, and aggregation of information. In particular, the invention is an apparatus designed to compile, store, transfer, retrieve, and/or aggregate electronic medically-related records.

The medical community has long sought a method for coordinating and analyzing aggregations of medically-related records. Technical difficulties have prevented the community from designing and implementing a system that permits computerized analysis of medical records. Because medical records are generally non-numerical expressions of concepts and because there is no uniform method of expressing those concepts, computers have traditionally lacked the capacity to recognize when a given medical record satisfies a query.

The community has attempted to design data structures that facilitate computerized classification of medical concepts. A proper data structure must balance the objectives of permitting concepts to be designed with a degree of expressivity, and of facilitating classification of concepts by limiting their complexity. Data structures in the prior art, however, have failed to provide the proper balance of expressivity and complexity to permit efficient coordination and retrieval of medical records.

Many data structures in the prior art lack adequate expressivity. They classify medical concepts according to an alphanumeric code organized in strict hierarchies. A strict hierarchy requires that a single concept have one meaning, one code number, and thus, only one parent concept. The concept must be positioned in one branch of a code-based hierarchical tree.

The SNOMED(™) International work of medical nomenclature is one example of a medical terminology structured according to a strict hierarchy. SNOMED International, which is incorporated herein by reference, is a systemized nomenclature of human and veterinary medicine, which is published, copyrighted and maintained by the College of American Pathologists. SNOMED International is an advanced nomenclature and classification of medical terms and codes.

SNOMED International, and its predecessor SNOMED, provide a detailed and specific coded vocabulary of names and descriptions used in healthcare. Their purpose is to index, store and retrieve information about a patient in a computerized medical record. The original SNOMED, published in 1974, consisted of six nomenclature categories or classes representing various aspects of the human being from a pathophysiologic point of view. These classes include, for example, topography (anatomy), morphology (descriptions of changes in the normal anatomy of the body), etiology (cause or causal agents of diseases or injuries, including drugs and chemicals), function (functions of the human body), disease/diagnosis (general and complex disease terms and syndromes), and procedures (administrative, preventive, diagnostic and therapeutic actions taken to prevent or cure).

Figure 8:
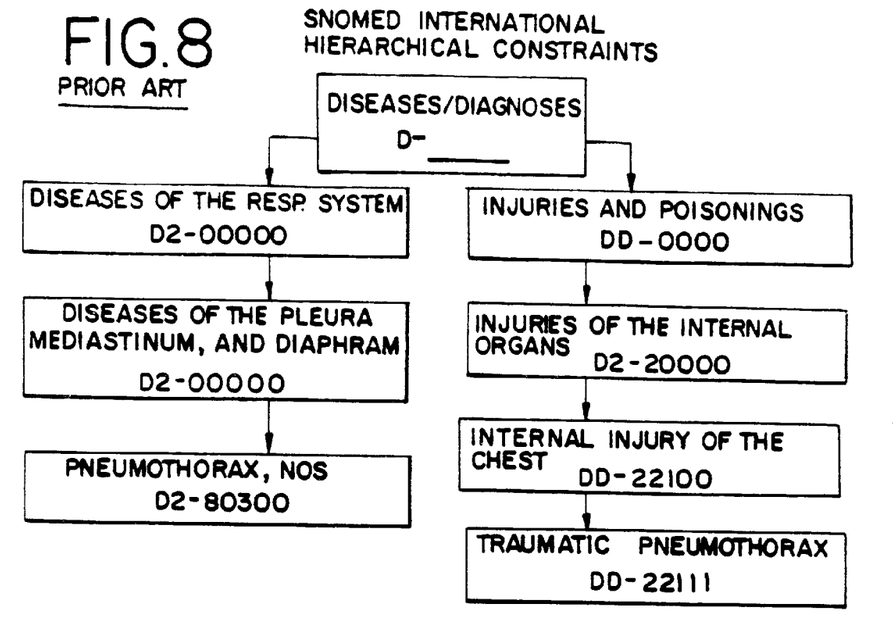
FIG. 8 schematically illustrates the hierarchical constraints of the data structure of the prior art known as SNOMED International; and, FIG. 9 schematically illustrates the data structure of the present invention without the hierarchical constraints of the prior art system of FIG. 8.
Figure 9:
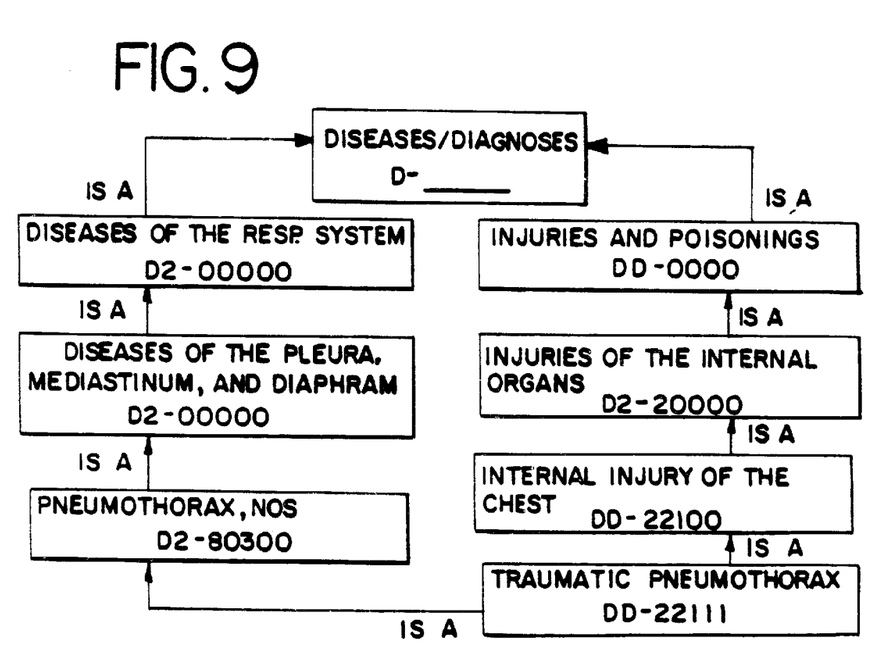

SNOMED International, published in 1993, expanded the nomenclature to 11 categories and provided some general linkage modifiers. SNOMED and SNOMED International have been licensed to numerous computer software vendors that have developed customized database applications. An example of the hierarchical constraints of SNOMED International are shown in FIG. 8, which illustrates the classification of the category of diseases by organ system or by the underlying etiology. The present invention, as described in more detail below, eliminates the strictly hierarchical constraints of SNOMED International. FIG. 9 illustrates one type of modification of the relationships of SNOMED International by the present invention.

Strict hierarchies based on alphanumeric codes provide less than satisfactory data structures for compiling, storing, transferring, retrieving, and/or aggregating medical records for two primary reasons. First, the data structure limits the efficacy of queries based upon hierarchical relationships, because medical concepts are complex ideas which are a function of the context of use, and therefore cannot be fully represented solely by a single code. Second, the data structure forecloses the user from forming queries based upon non-hierarchical relationships.

Strict hierarchical structures limit the ability of computers to search medical records according to hierarchical relationships because many medical concepts cannot be properly classified in a single position in a hierarchy. A term that can be described as belonging to several different groups must be encoded into one, and only one, group. One example is the term "pneumothorax. " Pneumothorax can be described as a member of the group of terms "diseases of the respiratory system," or a member of the group of terms "diseases of the pleura, mediastinum and diaphragm." In SNOMED International, for example, the term "traumatic pneumothorax" is classified in the class of "injuries and poisonings," with no link to the class of "diseases of the respiratory system."

A computer cannot satisfactorily search, sort and retrieve medical records that are organized according to a strict hierarchy. A query for a collection of records classified under a given parent term will not retrieve all pertinent records, when those records contain concepts that were constrained to be positioned in a separate branch of the hierarchy. In the above example, a query in SNOMED International for records of patients with diseases of the lung will not retrieve records of patients afflicted with traumatic pneumothorax, because traumatic pneumothorax was classified under "injuries and poisonings."

The prior art suffers from an additional limitation in that its data structures do not adequately permit users to search databases according to non-hierarchical queries. Strict hierarchies bundle the meaning of medical concepts into a single alphanumeric code. The code number expresses the relationship of the medical concept to other concepts along the same hierarchical axis, but fails to express the non-hierarchical characteristics of that concept. The code representing the medical concept does not provide information, for example, about how the concept manifests itself or how it is caused. Users cannot enter a query based upon non-hierarchical relationships when the meaning of a concept is contained only in a hierarchical code.

Some disclosed prior art database structures provide a limited ability to search medical records based upon non-hierarchical relationships. These systems, however, leave the meaning of the concepts based in an alphanumeric code, with non-hierarchical linking terms appended to the core meaning. These linking terms are not integrated into the meaning of the term, and do not explicitly define how the linking term relates to the core concept. For example, SNOMED International allows the concept "acute appendicitis" to be represented as an appendicitis that is acute, by allowing the user to select the alphanumeric code for the concept "appendicitis," with the alphanumeric code for the concept "acute." It remains unclear, however, whether the term "acute" refers to an appendicitis with an acute onset, or an appendicitis with an acute severity.

An ideal data structure for retrieval of medical records needs to offer limited complexity to properly process searches. A surfeit of linking terms restricts the ability of a computer to accurately process a query. The present invention addresses these concerns with a hierarchical structure that includes linkages between more specific child terms and less specific parent terms. At the same time, the present invention provides linkages along non-hierarchical axes or based on non-hierarchical relationships.

SUMMARY OF THE INVENTION

The foregoing limitations of prior art data retrieval systems are addressed by the following system for data retrieval of medical records.

The apparatus employs a terminology knowledge base with a data structure specifically designed to permit a classifier to execute subsumption checks upon a database of patient records. In one or more embodiments, the terminology knowledge base is a data structure containing representations of medical concepts. The concepts are formally defined in terms of their hierarchical and non-hierarchical relationships. Concepts are grouped into classes, with a different set of non-hierarchical relationships available to each class. Each concept is assigned an alphanumeric code.

Patient records are entered into a database of encoded clinical records. Each concept expressed in the patient records has an alphanumeric code that is the same as the alphanumeric code of the corresponding concept of the terminology knowledge base.

All concepts in the terminology knowledge base and patient database are expressed according to a description language based upon a set of four operators. This set of operators is sufficient to adequately represent medical concepts and to make inferences about the concepts for the purposes of the electronic medical record. Concepts are vertically linked along a common nomenclature axis in a hierarchical relationship. Concepts are also horizontally linked between different nomenclature axes in a non-hierarchical relationship. Concepts may be horizontally linked to one or more other concepts on different nomenclature axes.

A query manager receives queries and translates the queries into a format processible by the system. Queries are constructed using a standard description language. Queries need not be prespecified, and may seek information based upon hierarchical and non-hierarchical relationships. Queries are processed by a classifier which executes subsumption checks on the patient database to determine which patient records satisfy the query.

In one or more embodiments, the present invention comprises an apparatus for retrieving electronic records from a database of medical records. The apparatus utilizes a knowledge base in the form of a data structure set forth in a description language. The knowledge base includes representations of a plurality of concepts within a plurality of classes. For example, each of the concepts in a first class is vertically linked to another of the concepts in the first class by a parent hierarchical relationship. Each of the concepts in a second class is vertically linked to another of the concepts in the second class by a parent hierarchical relationship. Each of the concepts in a third class is vertically linked to another of the concepts in the third class by a parent hierarchical relationship.

Additionally, some of the concepts in the first class are horizontally linked to another of the concepts in the second class by a non-hierarchical relationship. One or more concepts in the first class are horizontally linked to another of the concepts in the third class by a non-hierarchical relationship.

In operation, a query manager receives a user query and translates the query into the description language. A records analyzer is coupled to the query manager, database and knowledge base. The records analyzer analyzes the records in the database based on the user query and the classes and the hierarchical and non-hierarchical relationships in knowledge base.

In one or more embodiments, the first class includes a plurality of concepts vertically linked in hierarchical relationships with other concepts in the first class, the second class includes a plurality of concepts vertically linked in hierarchical relationships with other concepts in the second class, and the third class includes a plurality of concepts vertically linked in hierarchical relationships with other concepts in the third class.

In one or more embodiments, each of a plurality of the concepts of the second class are horizontally linked to one or more of a plurality the concepts of the third class. The knowledge base can include additional classes, such as a fourth class including a plurality of concepts vertically linked with one another in a hierarchical relationship. Each of a plurality of the concepts of the third class are horizontally linked to one or more of a plurality of concepts of the fourth class. In one or more embodiments, the non-hierarchical relationships comprise a role relationship and the hierarchical relationships include parent relationships, child relationships, "is-a" relationships and "part-of" relationships.

In its preferred embodiments, each of the classes of the present invention comprises a nomenclature for medical terminology. The nomenclature for the classes is thus selected from one or more of the group of: (a) diseases/diagnoses, (b) morphology, (c) living organisms, (d) physical agents, activities and forces, (e) chemicals, drugs, and biological products, (f) social context, (g) topography, (h) bodily function, (i) procedures, (j) assessments, (k) spatial relationships,(l) substances, and (m) occupations. Additional classes are possible.

Each of one or more of this group of classes may have one or more associated role relationships. For example, the class of diseases/diagnoses has one or more associated role relationships from the group of: (a) etiology, (b) morphology, (c) course, and (d) severity. The class of topography has one or more associated role relationships from the group of: (a) part-of, (b) branch-of, and (c) tributary-of. Additional associated role relationships are possible.

These and other embodiments are explained in more detail below.

DETAILED DESCRIPTION OF THE PREFERRED EMBODIMENTS

The present invention relates to an apparatus and system for retrieving information stored in a database structure. The present invention has particular application as an apparatus for retrieving electronic medical records. The apparatus answers queries by determining which patient records are subsumed by the user's query.

The Database Processing System

Figures 1, 2:
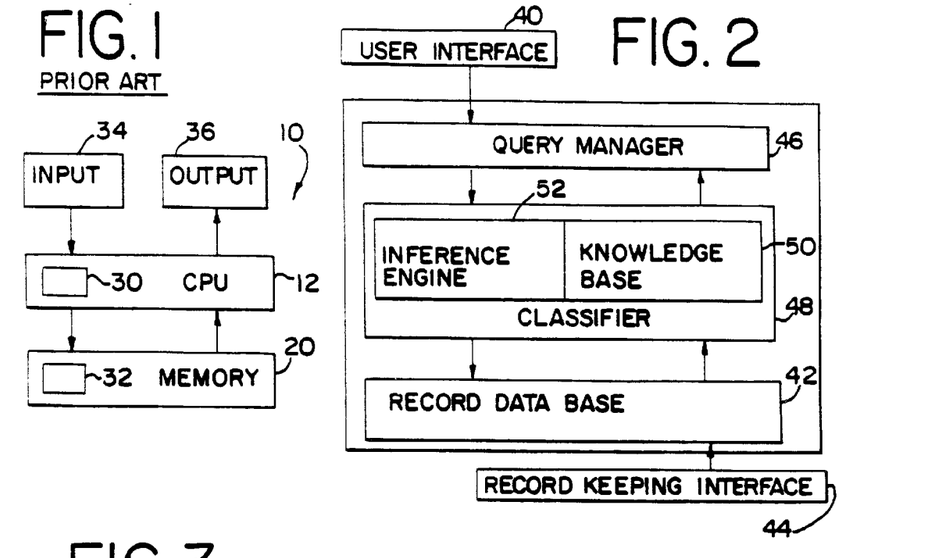
FIG. 1 schematically illustrates a conventional data processing system of the prior art for use with the present invention, including a central processing unit, memory and input and output devices.
FIG. 2 schematically illustrates the overall structure of the apparatus of the present invention including the classifier with inference engine and knowledge base.

FIG. 1 illustrates a conventional database processing system 10 for use in the apparatus or system of the present invention, which has a central processing unit (CPU) 12 and a memory 20. The CPU can be any standard and commonly known central processing unit, and memory 20 can include magnetic ROM and RAM as known in the art. Memory unit 20 may be connected to the CPU and user from a remote location. Application programs 30, 32 may be executed by the CPU. Operator input is possible through a keyboard 34 or other conventional input device. Output is viewed through a standard graphical user interface or terminal 36 or other known output device. The present invention utilizes this conventional database processing system for user interface with the query manager, knowledge base, inference engine and record database that form the apparatus of the present invention.

FIG. 2 illustrates the overall structure of the apparatus of the present invention. The user interface 40 includes the above-described input and output devices 34, 36. A record database 42 is stored in the memory device 20. Access to the record database for input of encoded records is possible through a record keeping interface 44.

Queries made to the database by the user are transmitted through a query manager 46. The query manager may utilize structured query language (SQL) or a similar type of query manager language. The apparatus includes a classifier 48 to process the queries and retrieve records responsive to the queries. The classifier includes both a knowledge base 50 and a inference engine 52, which will now be described in more detail. Reference will be made to the preferred embodiments of the present invention, which relate to a database structure for retrieval of medical records.

Knowledge Base

One component of the invention is a knowledge base. The knowledge base is a data structure containing representations of medical concepts. All concepts are formally defined in terms of the relationships of the concepts with other concepts in the knowledge base.

The concepts are defined according to two kinds of relationships. One kind of relationship is hierarchical, based on whether a concept is a type of (is subsumed by) another concept. The subsuming concept is called a "parent." The hierarchical relationships express the set of parents of a concept. All concepts have at least one parent, and concepts can have multiple parents. Concepts in a hierarchical relationship are vertically linked along a nomenclature axis or axes within a single nomenclature category or class. The hierarchical relationships are transitive. That is, if A is a parent of B, and B is a parent of C, then A is also a parent of C.

Concepts are also defined by their non-hierarchical relationships. These non-hierarchical relationships describe the differentiating, essential characteristics of a concept, which include a name for the relationship, called a "role"; and a value, called a "role restriction." Roles are typically related relationships or attributes of a concept. The essential characteristics express those aspects of a concept that are inherent and essential to the meaning of the concept, and that differentiate the concept from similar concepts. Concepts in non-hierarchical relationship are horizontally linked to separate nomenclature categories or classes by their essential characteristics.

Concepts are therefore grouped into nomenclature categories or classes. Each class of concepts has a format described by a foundational model. A foundational model is a set of roles that are available to be used to form essential characteristics that define members of the class of concepts. A set of foundational models, with the roles that are available in each foundational model, are specified below. For example, the class or nomenclature category of concepts called assessments (the disease/diagnosis that describes the condition) has a series of roles or attributes, such as the associated etiology (the causative agent) and the associated morphology (change at the tissue level), that horizontally link the concept to a separate nomenclature category or class. The role restriction may be concept in the separate class.

Semantics express the meaning of the roles and their application in ordinary language. The semantics of each role are specified below.

Every concept has an alphanumeric code. The code is an arbitrary identifier used to represent the concept in a repository of patient records and in the knowledge base.

To create the terminology knowledge base, human modelers represent medical concepts according to the above hierarchical and non-hierarchical relationships and their associated semantics. The modelers provide representations for general concepts as well as specific concepts. The modelers assign an alphanumeric code to each concept. The resultant set of medical concepts comprises the terminology knowledge base.

Description Language

All concepts in the knowledge base are expressed according to a description language. The description language of the invention is based upon a set of four operators. This is the set of operators that are sufficient to adequately represent clinical concepts and to make inferences about the concepts for the purposes of compiling, storing, retrieving, transferring, and/or aggregating electronic medical records. The set of operators allows modelers to represent concepts using the proper combination of expressivity and limited complexity.

The set of operators is comprised of the following four: top, bottom, conjunction, and exists restriction. A "top" operator implies that it is the parent of all concepts. A "bottom" operator implies that it is the child of all concepts. A "conjunction" operator implies that concepts may be conjoined by an "and" conjunction. An "exists restriction" operator corresponds to the existential quantification operator in predicate logic.

General Operation of the Record Retrieval Apparatus

Figure 3:
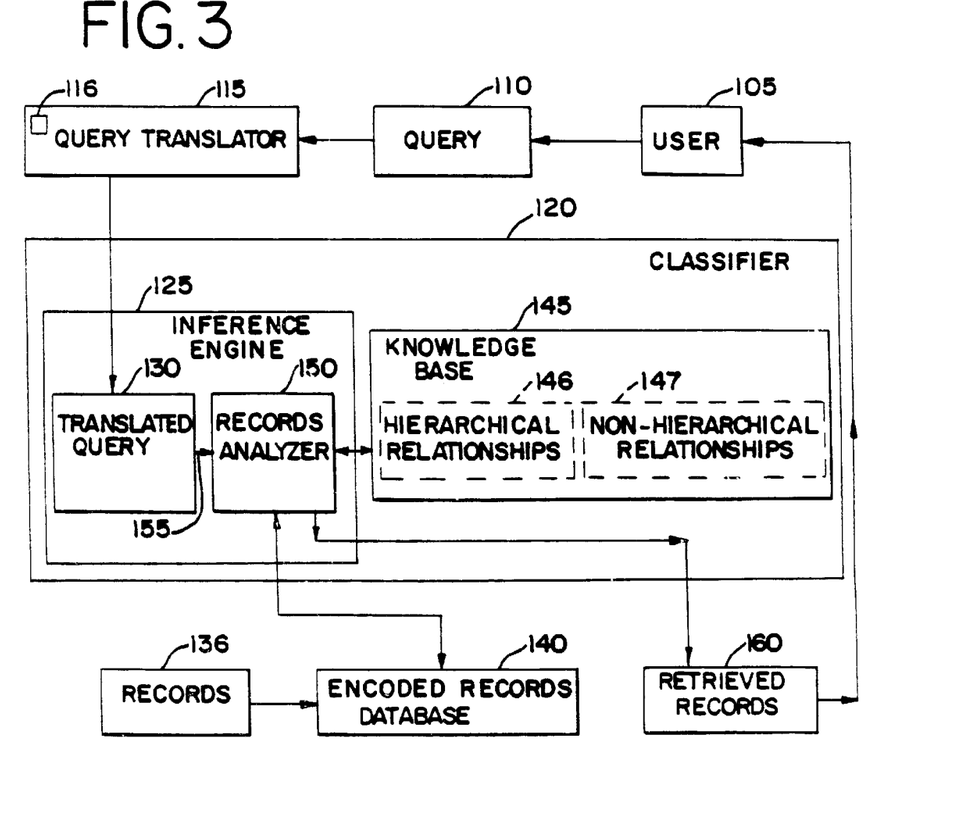
FIG. 3 schematically illustrates the overall process for record retrieval of the present invention.

A general schematic illustrating the overall process for record retrieval is depicted in FIG. 3. User 105 enters a query 110. The query 110 is translated in a query translator 115. The query must be translated and expressed according to description language 116.

The translated query 130 is sent to the classifier 120 for subsumption checking. Within the classifier 120, the translated query 130 is sent to the inference engine 125.

The inference engine 125 undertakes a records analysis by identifying or searching through encoded patient records that are located in the encoded patient records database 140. Patient records 136, or other raw data, have been previously encoded and stored in an encoded patient records database 140. The encoded records database is searched and reviewed, or subjected to records analyzer 150. The details of the software utilized to encode the records for the encoded records database and to search and review the encoded records database based on the translated query is known by those skilled in the art and not the subject of the present invention.

The inference engine 125 analyzes the records in the encoded patient records database 140 based on input from the translated query 130 and input from the knowledge base 145. The definitions contained in knowledge base 145 are expressed according to description language 116. The data structure in the knowledge base 145 comprises a set of concepts that are interlinked by hierarchical and non-hierarchical relationships 146, 147.

Figure 4:
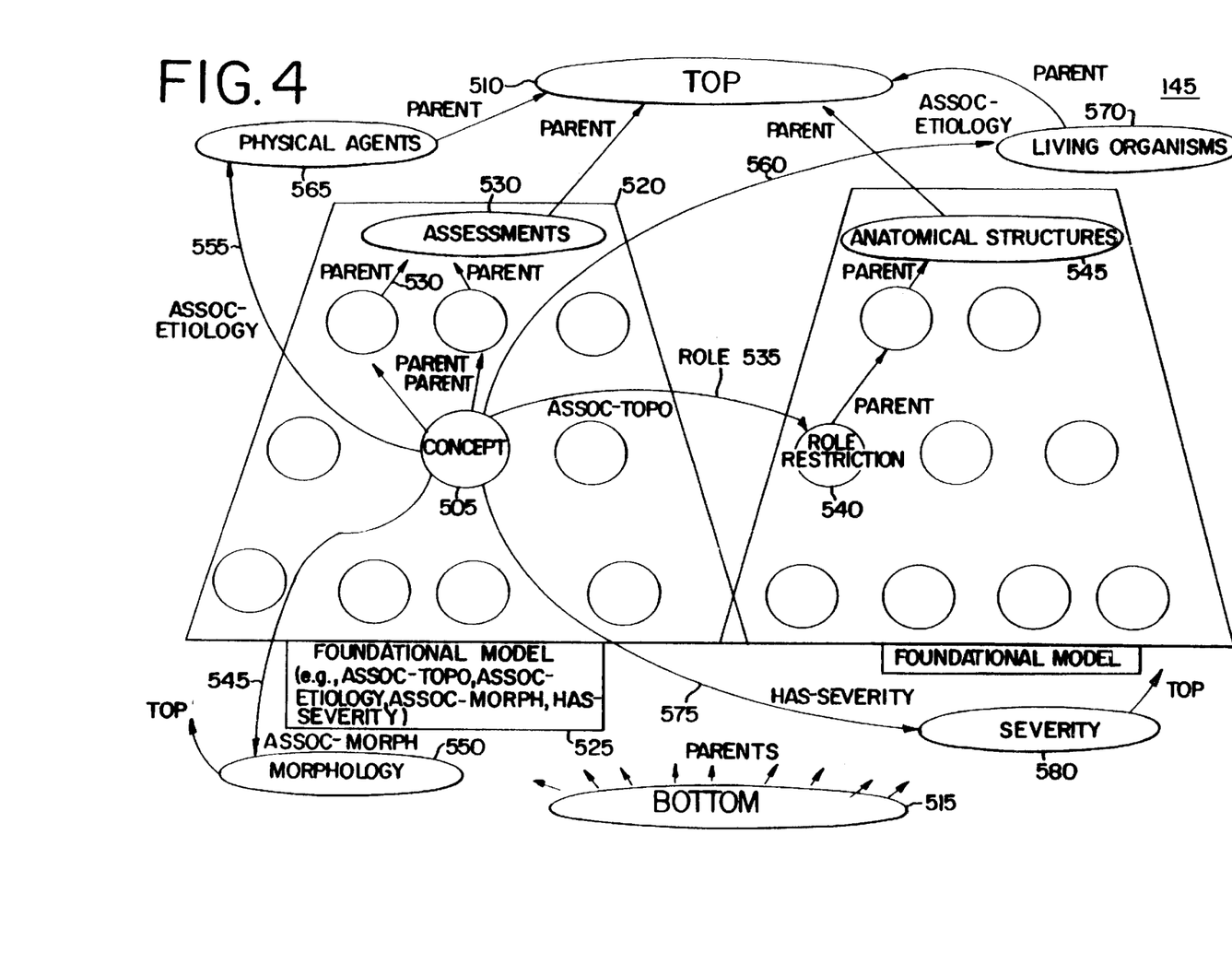
FIG. 4 schematically illustrates the details of a portion of the knowledge base of the present invention, including concepts in hierarchical relationships within classes and concepts in non-hierarchical relationships between classes.

The knowledge base 145 contains a data structure shown in more detail in FIG. 4. The data structure comprises a set of concepts, wherein a typical concept is represented by concept 505. One of the concepts, top 510, is the parent of all concepts. Top 510 has no parents. One concept, bottom 515, is the child of all concepts. The remaining concepts are grouped into categories or classes that are arranged in hierarchies, such as class 520. The hierarchies represent relationships between classes or concepts. The knowledge base contains one or more hierarchies, and so may be termed a polyhierarchical knowledge base.

Each concept has one or more parent concepts (excepting top 510, which has no parents). A concept is vertically linked to its parents by hierarchical parent-type relationships 530. Concepts may be horizontally linked to other concepts in other classes by one or more non-hierarchical relationships.

Each class is based upon a foundational model 525. The foundational model is a set of allowable roles for concepts in that class. Roles are the non-hierarchical relationships that concepts in a given class may have with concepts in another class or classes. There is no restriction on the number of non-hierarchical relationships that a concept can have, but the number of different kinds of roles that a concept in a given class can have are strictly limited by the available roles of the foundational model 525 for that class. Roles create a horizontally linked or non-hierarchical relationship between a concept 505 in one class with another concept, called a role restriction 540, in another class.

In the preferred embodiment of the invention, which relates to medical records terminology, one class is a hierarchy of assessments 530. Assessments are the class of concepts of diseases or diagnoses that describe a given condition. The foundational model 525 of the assessments class 530 can have, for example, roles for associated topography, associated-etiology, associated morphology, and has-severity.

The role for associated-topography provides a non-hierarchical link 535 to a role restriction or concept 540 in the separate class or hierarchy for anatomical structures 545. The role for associated-morphology, similarly, can provide a non-hierarchical link 545 from concept 505 to a role restriction or concept in the morphology class 550. The role for associated-etiology can provide links 555 and 560 from concept 505 to role restrictions in the classes for physical agents 565 and living organisms 570. The role for has-severity can provide a link 575 from concept 505 to the severity class 580.

Based on the hierarchical and non-hierarchical relationships between concepts in the knowledge base, the encoded records are analyzed in the records analyzer 150. The inference engine 125 compares the translated query 130, with the patient records in the defined patient records analyzer 150. This comparison is called a subsumption check 155, and determines whether the defined patient record is subsumed by, or matches, translated query 130.

If the translated query 115 subsumes the defined patient record, a notation of the record is passed to the retrieved records collector 160. Records in the retrieved records collector 160, which satisfy the query, are returned to the user 105.

Operation of Record Retrieval Apparatus With Patient or Other Medical Records Database Physicians and other health care professionals create electronic records that represent the health records of their patients or other medically related records. The physicians and other professionals may either manually express patient or other medically-related records in terms of codes and expressions processable by the invention, or an interface may translate narrative patient records into codes and expressions processable by the invention.

The resulting set of electronic records comprises a database of records. The alphanumeric codes used in the patient/medical database are the same as the alphanumeric codes of the corresponding concepts of the terminology knowledge base. The expressions used in the database of patient records use the same description language as the expressions used to define concepts in the terminology knowledge base.

The invention has particular application as a data structure that permits the efficient linking of medical concepts. The data structure is composed of data attributes that represent medical concepts. The medical concepts are represented by a term which is categorized in one of ten or more classes of medical terminology. The classes include:

(1) diseases/diagnoses;
(2) morphology;
(3) living organisms;
(4) physical agents, activities, and forces;
(5) chemicals, drugs, and biological products;
(6) social context;
(7) topography;
(8) etiology (cause of disease)
(9) function;
(10) procedures;
(11) spatial relationships;
(12) assessments;
(13) substances, and
(14) occupations.

The classes are defined in terms of hierarchical and "essential characteristics" relationships with other concepts or classes. The concepts are defined using hierarchical relations that describe the relationship of the concept with other concepts of the same hierarchy or class. The concepts are also defined by "essential characteristics" relations that describe the essential characteristics of the concept with concepts contained in separate hierarchies or classes.

The invention permits modelers to assign hierarchical relationships between on or more classes. The purpose of the hierarchical links is to define the relationships of an attribute with other attributes within the same hierarchy. One hierarchical relation is that of parent/child. A child can have more than one parent. A parent can have more than one child.

The invention then defines these parent/child relationships with description logic terms. One way is to use an "Is-A" relation, whereby it is stated that an attribute "is a" child of a parent. For example, pneumonia "is a" disease of the lung. Another way is to use a "Part-Of" relation, whereby it is stated that a child is a "part of" a parent. For example, an iris is a "part of" an eye. Hierarchical relationships are used only within a given class.

This embodiment of the invention also permits modelers to assign "essential characteristics" relationships to a condition. The purpose of the "essential characteristics" links is to describe the essential characteristics of a medical condition. The "essential characteristics" relationships are based on the class categories:

the disease/diagnosis and/or assessment that describes the condition;
the morphology of the condition or descriptions of the changes in anatomy, such as tissues;
the living organisms that cause the condition;
the physical agents, activities, and forces that cause the condition;
the chemicals, drugs, and biological products that cause the condition or that can be used to treat the condition;
the social contexts that cause the condition;
the topography in which the condition is located;
the bodily functions that the condition affect;
the spatial relationships of the body;
the normal and abnormal substances relating to the condition;
the procedures used to treat the condition; and
the occupation of the patient affected by the condition.
the etiology or cause of the condition These relationships are denoted by description logic terms. One example of a description logic term is (assoc-topography), which describes the topography in which a condition is located.

Modelers define all the attributes of the classes in terms of their relationships with other attributes. The meaning of a term is determined by its relational table. The relational table contains all relationships—both hierarchical and "essential characteristics"—of a given condition. The relational table is governed by description logic.

With the above-described hierarchies set forth in the knowledge base, a user can enter a query into a computer to seek one or more records from the patient medical database that are subsumed by (i.e., match) the query. The user may enter the query in one of a number of formats, which may include natural language and do not form part of the present invention. The query is received by a query manager, which translates the query into a format processible by the invention.

Queries are constructed using the description language used for the terminology knowledge base and for the patient medical database. Users can enter a variety of queries. The queries need not be prespecified. One kind of query may seek patient records that have hierarchical relationships with the information sought.

As an example, a researcher may enter a query to identify all patients with a disease of the lung. Because pneumonia is a disease of the lung according to the hierarchy represented in the terminology knowledge base, the invention will match pneumonia with the query for "diseases of the lung," and return the records of all patients whose records include a description language expression indicating they have pneumonia.

Also, a user might enter a query seeking records having a certain role restriction for a role. For example, a user might enter a search for all records related to diseases that manifest themselves in inflammation of the larynx. The query would specify that the disease must have "inflammation" as the role restriction for its associated morphology (assoc-morph) role, and must have "larynx" as the role restriction for its associated topography (assoc-topo) role. Because laryngitis is a disease that manifests itself in inflammation of the larynx, the invention will return all records denoting laryngitis.

Each of the preferred embodiments of the invention contains a classifier that processes the query. In the medical terminology embodiment, the classifier receives the query and executes subsumption checking of each patient/medically-related record based upon the terminology knowledge base, to determine which recorded entries in patient/medically-related records are subsumed by the query.

The classifier determines which records of the patient/medical database are subsumed by a query. To do this, the classifier executes a subsumption check on the records, based on the terminology knowledge base. The classifier identifies which concepts in the patient/medically-related record are subsumed by the query. That is, it identifies which concepts in the record have characteristics that are sufficient to satisfy the criteria sought by the user. The classifier notes the alphanumeric codes of those concepts subsumed by the query. The classifier then returns to the user all patient records that have concepts subsumed by the query.

All concepts must be expressed in the description language of the invention. Several formats permit expression of the concepts. One permissible format is to express the concepts in logical sentences conforming to the description language of the invention. A second permissible format is to express the concepts in tables that express all the hierarchical and non-hierarchical relationships of the concepts.

The invention has a plurality of foundational models. These include foundational models for assessments (diseases, diagnoses, etc.), anatomical structures, and procedures. Each of these foundational models is a set of roles that are available to specific instances of each class of concepts. Each role is defined by semantics. Following is a list of roles and semantics for the foundational models of the presently preferred embodiments:

Diseases/Diagnoses (Assessments)
   administers-energy
      Energy applied to, placed into, or transmitted through the body with the intent of achieving a therapeutic, prophylactic, protective, diagnostic, nutritional, and/or physiological goal.
   assoc-etiology
      The direct causative agent (e.g., organism, toxin) of the disease or disorder.
      Does not include vectors, such as the mosquito that transmits the malaria.
      Does not include method or mechanism by which the etiology is introduced to the body.
   assoc-morphology
      The morphologic change seen at the tissue or cellular level, affected by the disease or disorder.
      Refers to the primary subject of the disease concept.
   assoc-topology
      The anatomic site affected by a condition or a procedure, or the affected site resulting in a condition.
   has-course
      The time course of the disease or assessment, usually expressed as acute, subacute, or chronic.
   has-severity
      The severity of the disease or assessment, which may be expressed as mild, moderate, severe, and also may be expressed as acute.

Procedure
   administered-substance
      A chemical placed into the body or a non-inert material placed onto the body that is meant to interact chemically with the intent of achieving a therapeutic, prophylactic, protective, diagnostic, nutritional and/or physiological goal.
   assoc-topo
      The site affected by a condition or a procedure, or the affected site resulting in a disorder.
   has-object
      The object of a procedure is that thing to which the root operation of the procedure is directed towards. The goal or object of a procedure.
   uses-equipment
      Defines the material used to accomplish a procedure.
Laboratory test roles
   has-measured-component
      Substance or thing or physiological or physical function being measured.
   has-method
      The method by which a procedure is performed.
   has-property
      the kind of quantity being measured.
   has-scale-type
      The scale of the result of an observation of a diagnostic test.
   has-specimen
      The bodily source.
   has-subject-of-observation
      Distinguishes observations or actions on the patient from observations or actions on non-patient materials that relate to the patient.
   has-time-aspect
      Definitional temporal relationships for a procedure.

Anatomical Structures
   part-of
      For indicating inclusion of one structure entirely within another structure (e.g., the right atrium is part-of the heart).
   branch-of
      A role for indicating relationships between structures that are not part of each other, but are connected to each other, with one structure branching from the other. Particularly for use with arteries and nerves.
   tributary-of
      A role for indicating relationships between structures that are not part of one another, but are connected to each other, with one structure feeding into the other. Particularly for use with veins and lymphatics.

The invention can employ one of a number of suitable classifiers known in the art. Suitable classifiers include K-REP and ONTOLOG. The invention can employ one of a number of suitable syntaxes. In its preferred embodiment, the invention employs KRSS, which is known in the art. Other suitable syntaxes include K-REP syntax and ONTOLOG syntax.

Example I of Medical Record Retrieval

Figure 5:
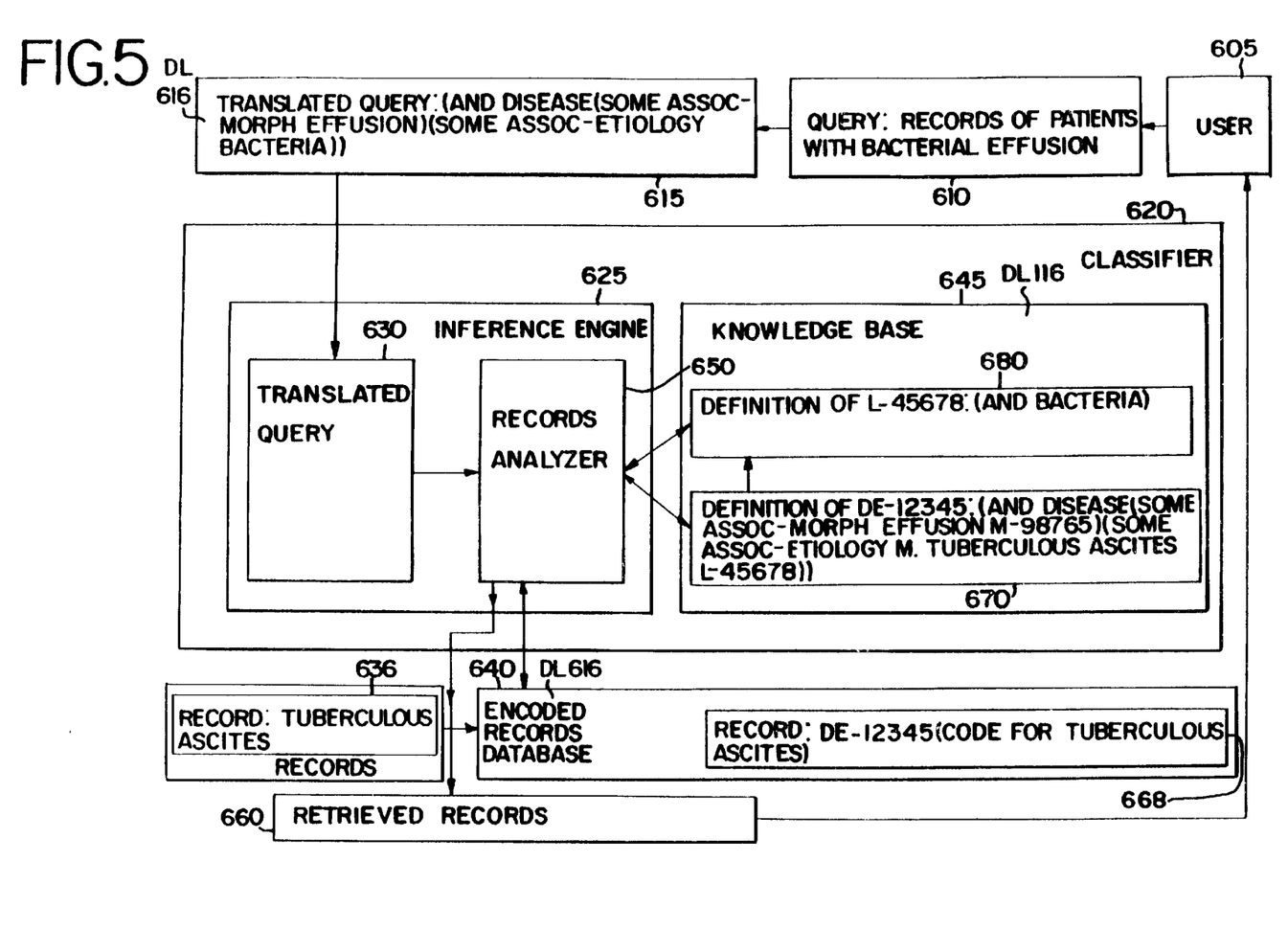
FIG. 5 schematically illustrates an example of record retrieval in one embodiment of the present invention.

FIG. 5 provides a specific example of how the apparatus can retrieve medical records. User 605 enters a query 610, seeking a collection of records for medical patients afflicted with a bacterial effusion.

The query is translated into description language 616, in the query translator 615. The translated query 630 becomes the following expression: (and disease (some ASSOC-MORPH effusion) (some ASSOC-ETIOLOGY bacteria)). The expression means that the query seeks records containing a concept that is a disease, and that manifests itself (has morphology) in an effusion, and that is caused by (has etiology) bacteria.

The query is sent to classifier 620, and within the classifier to inference engine 625. Inference engine 625 then searches encoded records, which have been previously stored in the encoded records database 640. Encoded records may include, for example, record 668 for tuberculous ascites, with code number DE12345.

The inference engine finds the definition for DE12345 (tuberculous ascites) in knowledge base 645. In this example, definition 670 of DE12345 is the following expression: (and disease (some ASSOC-MORPH effusion M-98765) (some ASSOC-ETIOLOGY M.Tuberculous Ascites L-45678)). Definition 670 is compared in records analyzer 650 with translated query 630. The role of definition 670 for ASSOC-MORPH effusion matches (is subsumed by) query 615, which seeks ASSOC-MORPH effusion.

The role of definition 670 for ASSOC-ETIOLOGY, M.Tuberculous ascites L-45678, is not directly subsumed by query 615, because the query seeks ASSOC-ETIOLOGY bacteria. Inference engine 625 then checks knowledge base 645 for the definition of M-Tuberculous ascites L-45678. Knowledge base contains definition 680 stating that M.tuberculous ascites L-45678 has parent "bacteria." Inference engine 625 executes another subsumption check, finding that query 615 for ASSOC-ETIOLOGY bacteria does subsume record 668, because M-Tuberculous ascites has parent "bacteria."

Because record 668 is subsumed by translated query 630, inference engine sends a notation of record 668 to retrieved records collector 660, which sends collected records back to user 605.

Example II of Medical Record Retrieval

Figure 6:
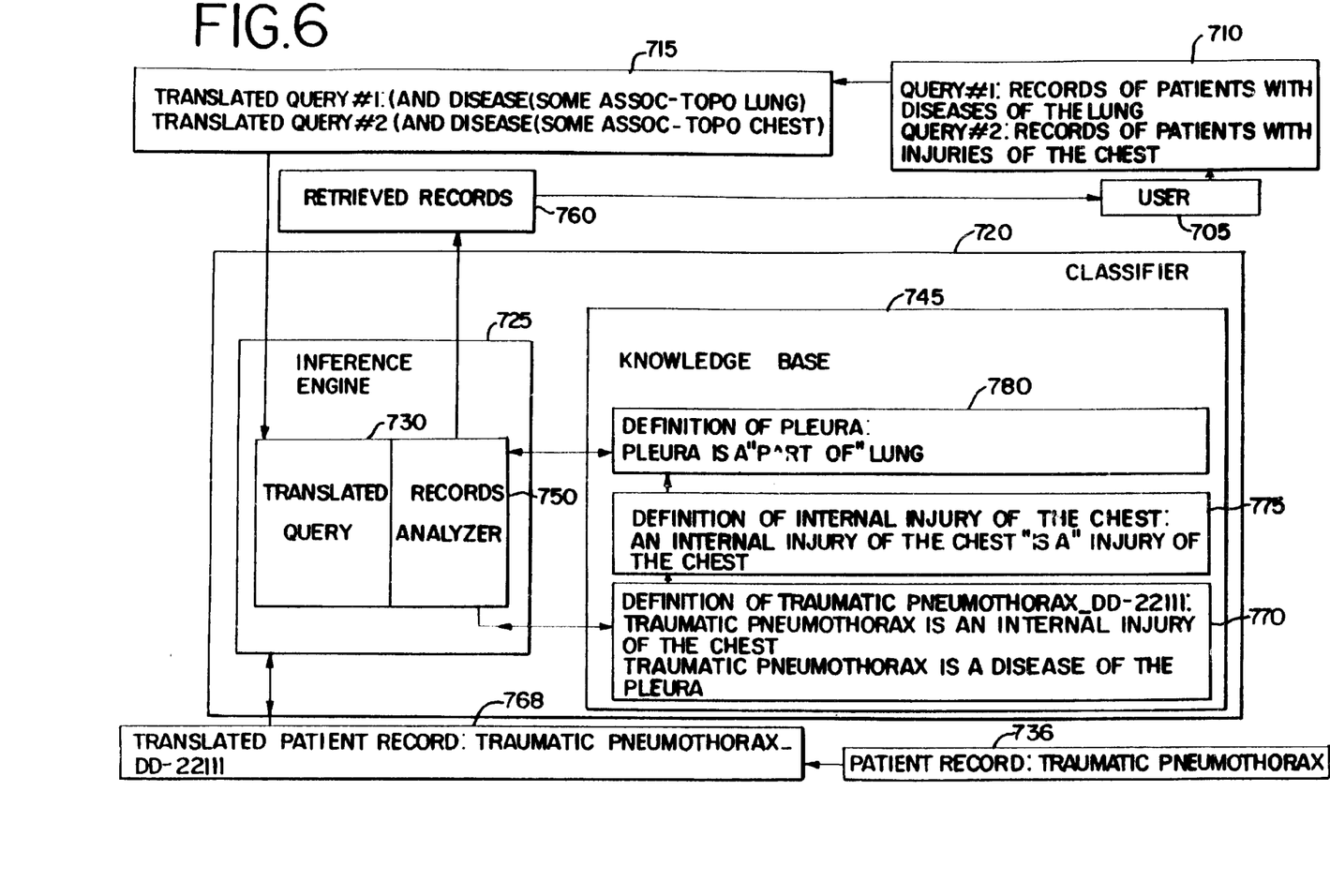
FIG. 6 schematically illustrates a second example of record retrieval in one embodiment of the present invention, which inputs multiple queries.

FIG. 6 provides a specific example of how the apparatus can retrieve medical records for multiple queries. User 705 enters a plurality of queries 710, seeking a collection of records for medical patients afflicted with diseases of the lung and injuries of the chest.

The queries are translated into description language in the query translator 715. Translated Query #1 becomes the following expression: (and disease (some ASSOC-TOPO lung)). The expression means that the query seeks records containing a concept that is a disease, and that is located (has topography) in the lungs. Translated Query #2 becomes the following expression: (and disease (some ASSOC-TOPO chest)). The expression means that the query seeks records containing a concept that is a disease, and that is located (has topography) in the chest.

The queries are sent to classifier 720, and within the classifier to inference engine 725. Inference engine 725 then searches encoded records, which have been previously stored in the encoded records database. Encoded records may include, for example, record 768 for traumatic pneumothorax, with code number DD-22111.

The inference engine finds the definition for DD-22111 (traumatic pheumothorax) in knowledge base 745. In this example, definition 770 of DD-22111 includes the following expressions: Traumatic Pneumothorax is an Internal Injury of the Chest; Traumatic Pneumothorax is a Disease of the Pleura.

Definition 770 is compared in records analyzer 750 with translated queries 730. The role of definition 770 for ASSOC-TOPO lung and ASSOC-TOPO chest, Traumatic Pneumothorax DD-22111 matches (is subsumed by) query 715. The inference engine 725 checks the knowledge base 745 for the definition of Traumatic Pneumothorax DD-22111. Knowledge base 745 contains definition 775 stating that Internal Injury of the Chest "Is-A" injury of the chest. Knowledge base 745 also contains definition 780 stating that a Pleura is a "Part-Of" the lung. Inference engine 725 executes a subsumption check and finds that query 715 for ASSOC-TOPO lung and ASSOC-TOPO chest does subsume record 768 because it is an injury of the chest and is a disease of part of the lung."

Because record 768 is subsumed by translated query 730, inference engine sends a notation of record 768 to retrieved records collector 760, which sends collected records back to user 705.

Example III of Medical Record Retrieval

Figure 7:
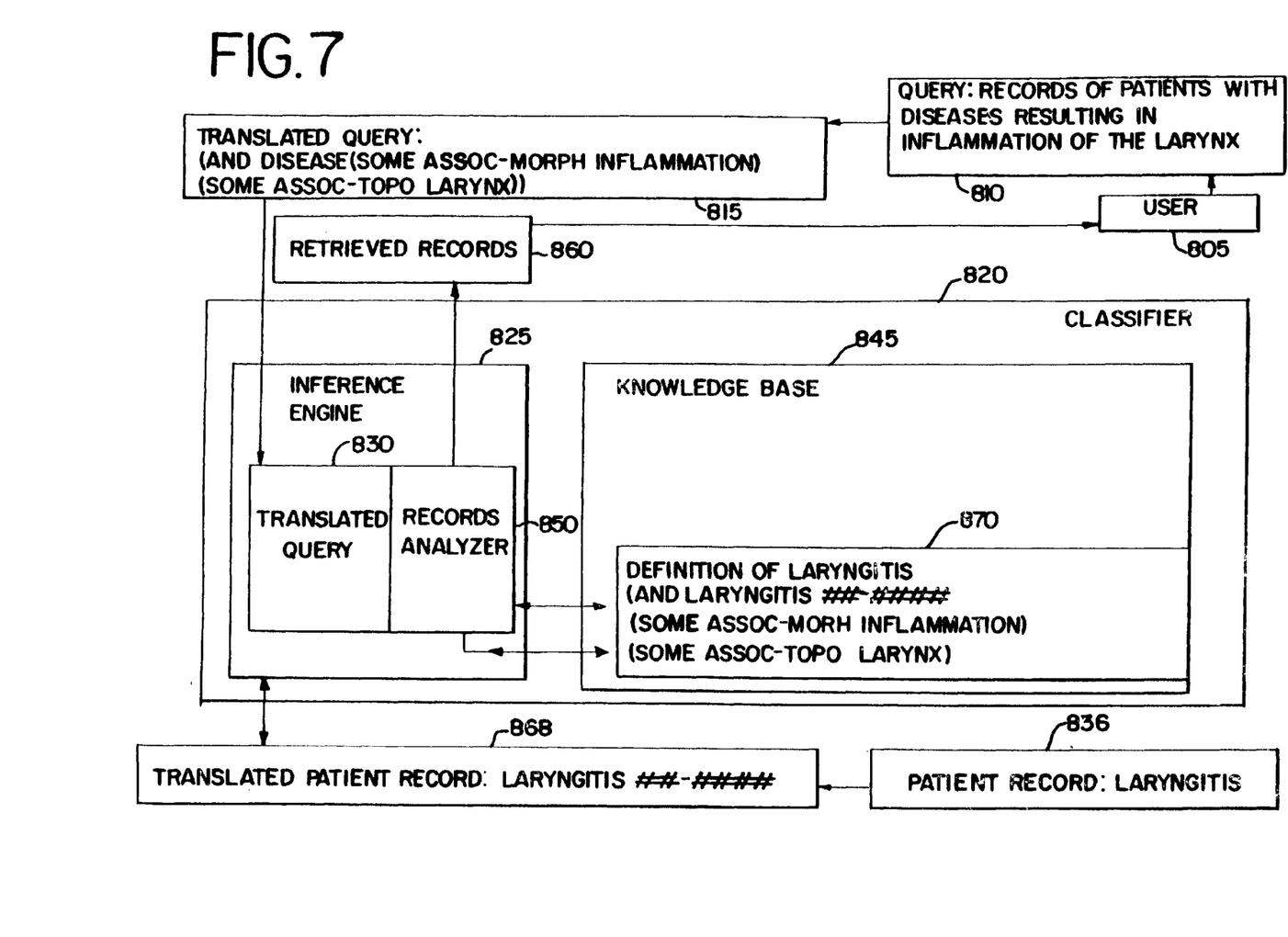
FIG. 7 schematically illustrates a third example of record retrieval in one embodiment of the present invention, which undertakes subsumption checks based on non-hierarchical roles.

FIG. 7 provides a specific example of how the apparatus can retrieve medical records for queries that require subsumption checks based upon non-hierarchical roles. User 805 enters query 810, seeking a collection of records for medical patients afflicted with diseases resulting in inflammation of the larynx.

The queries are translated into description language in the query translator 815. The translated query becomes the following expression: (and disease (some ASSOC-MORPH inflammation) some (ASSOC-TOPO larynx)). The expression means that the query seeks records containing a concept that is a disease, and that manifests itself (has morphology) in inflammation and that is located (has topography) in the larynx.

The query is sent to classifier 820, and within the classifier to inference engine 825. Inference engine 825 then searches encoded records, which have been previously stored in the encoded records database. Encoded records may include, for example, record 868 identifying a patient with laryngitis.

The inference engine finds the definition of laryngitis in the knowledge base 845. In this example, definition 870 of laryngitis includes a non-hierarchical link to role restriction ASSOC-MORPH inflammation, as a disease that manifests itself as an inflammation. Definition 870 of laryngitis also includes a non-hierarchical link to role restriction ASSOC-TOPO larynx, as a disease that is located in the larynx.

Definition 870 is compared in records analyzer 850 with translated query 830. The definition 870 for laryngitis with role restriction ASSOC-TOPO larynx and ASSOC-MORPH inflammation, matches (is subsumed by) query 815.

Because record 868 is subsumed by translated query 815, inference engine sends a notation of record 868 to retrieved records collector 860, which sends collected records back to user 805.

Advantages of the Data Structure of the Knowledge Base

The data structure of the terminology knowledge base enables the classifier to perform subsumption checks. The data structure imposes a multidimensional physical organization upon the concepts of the terminology knowledge base that allows the classifier to determine which concepts are subsumed by the query.

The apparatus can process queries that rely on hierarchical and non-hierarchical relationships of the concepts. The ability of the apparatus to retrieve concepts based on hierarchical links is due to the transitive nature of the hierarchical links. The transitive nature of the hierarchical links allows the classifier to identify all instances of a set of concepts that satisfy the query, no matter how many levels of generality separate the instance from the queried concept.

Subsumption checks based on hierarchical relationships are more effective in the present invention than in the prior art because the data structure of the knowledge base of the present invention permits concepts to have more than one parent term. For example, a term such as traumatic pneumothorax can have parents such as "diseases of the respiratory system" and "injuries and poisonings." The ability to assign more than one parent term to a concept permits the invention to return all instances of a queried class of concepts. A user can search upon any one of a child concept's parent concepts in order to return medically related records denoting diseases modeled by that child concept. For example, a researcher seeking records of patients afflicted with "traumatic pneumothorax" can search under either "diseases of the respiratory system" or "injuries and poisonings," because traumatic pneumothorax is represented as having both these parents.

Systems of the prior art do not permit this flexibility. For example, in SNOMED International, the term "traumatic pneumothorax" had to be grouped under either "diseases of the respiratory system" or "injuries and poisonings." It was assigned to the latter. A researcher using SNOMED International who entered a query seeking records of patients afflicted with diseases of the respiratory system would not receive records of patients with traumatic pneumothorax.

The invention can also perform subsumption checking based on non-hierarchical relationships. Subsumption checks based on non-hierarchical relationships are more effective in the present invention than in the prior art due to the structure of the knowledge base. In the knowledge base of the present invention, non-hierarchical relationships are explicitly expressed in terms of roles and role restrictions in order to unambiguously establish the meaning of the relationships. Users of the invention can execute searches upon these roles and role restrictions without ambiguity.

For example, the concept "acute appendicitis" can be ambiguous as to whether the acuteness refers to the severity or the onset of the appendicitis. The present invention will assign the role restriction "acute" to either the role "has-severity" or "has-course" to express whether the concept represents an appendicitis with an acute severity or an appendicitis with an acute onset, respectively. A researcher seeking records of patients afflicted with appendicitis characterized by a fast onset can search for patients afflicted with an appendicitis that "has-course acute." In the prior art, terms such as "acute" were not assigned as restrictions to roles such as "has-severity" and "has-course." Researchers thus could not distinguish between cases of appendicitis with acute severity and acute onset.

This embodiment of the invention surpasses the capabilities of the prior art database structure known commercially as SNOMED International because it permits greater flexibility in linking terms hierarchically. SNOMED International assigned one, and only one, code number to a given medical term. This code number gave meaning to the term by identifying the position the term occupied in a strict hierarchy of terms. SNOMED International declined to give more than one code number to a medical term in order to avoid ambiguity in the meaning of the term. This strict hierarchical system, however, limited the ability of modelers to accurately describe medical terms. At finer levels of specificity, a medical condition might be equally well positioned under two different hierarchical trees, forcing the modelers to choose between one or the other. Modelers were thus precluded from including conditions in hierarchical trees where researches might search for the condition, thus limiting the utility of SNOMED as a data structure.

This invention addresses this problem by moving the meaning of a term from a lone code number to a relational table which contains all relations the term has with other members of its hierarchy. Modelers are not required to place a medical term in one hierarchical tree or another, but are free to ascribe to a term all the hierarchical relationships that characterize it.

The present invention also surpasses the capabilities of SNOMED International by including "essential characteristics" relationships in the meaning of the medical term. In SNOMED International, the meaning of the medical term is included solely in its assigned code number. Although SNOMED International offered general links to describe the medical term in relation to medical terms from other hierarchies, these links are not included in the core meaning of the term, and are not computer processable. Researchers are precluded from searching the database according to linking terms. The linking terms, although useful at the doctor level for describing the conditions of individual patients, are not useful at the modeler level for advancing the research capabilities of the database.

This invention addresses this problem by incorporating "essential characteristics" links into the core meaning of the medical condition. The "essential characteristics" terms are included in tandem with the hierarchical links discussed above. Because the "essential characteristics" links become part of the core meaning of the term, they are computer readable, and facilitate cross-hierarchy research.

Non-hierarchical relationships also provide benefits in clarifying the contextual definitions of concepts that use the same term. For example, an "iris" is a flower that can cause irritations and also is a part of an eye. With non-hierarchical relationships iris is defined to be "part of" the eye and also "is a" flower.

Strict hierarchies also impose limitations upon the expansion of the data structure to accommodate growth of medical knowledge. The present invention permits expansion and reorganization of the data structure to incorporate new hierarchies.

What is claimed is:

1. An apparatus for retrieving electronic records from a database of medical records, comprising:

a database of medical records;

a knowledge base having a data structure set forth in a description language, said knowledge base including a plurality of classes having a plurality of concepts, each of said classes comprising a nomenclature for medical terminology, each of said concepts in a first class being vertically linked to another of said concepts in said first class by a hierarchical relationship, each of said concepts in a second class being vertically linked to another of said concepts in said second class by a hierarchical relationship, each of said concepts in a third class being vertically linked to another of said concepts in said third class by a hierarchical relationship; said hierarchical relationships including parent relationships, child relationships, "is-a" relationships and "part-of" relationships; said nomenclature for said classes being selected from one or more of the group of: (a) diseases/diagnoses, (b) morphology, (c) living organisms, (d) physical agents, activities and forces, (e) chemicals, drugs, and biological products, (f) social context, (g) topography, h) human bodily function, (i) treatment procedures, (j) etiology, (k) spatial relationships, and (l) occupations;

a plurality of said concepts in said first class being horizontally linked to a plurality of said concepts in said second class by non-hierarchical relationships, a plurality of said concepts in said first class being horizontally linked to a plurality of said concepts in said third class by non-hierarchical relationships; each of said non-hierarchical relationships further comprises a role relationship;

a query manager that receives a user query and translates said query into a description language; and a records analyzer coupled to said query manager, said database and said knowledge base; said records analyzer analyzing said records in said database based on said user query and said classes and said hierarchical and said non-hierarchical relationships in said knowledge base.

2. The apparatus of claim 1 wherein each of a plurality of said concepts of said second class are horizontally linked to each of a plurality of said concepts of said third class, said knowledge base having a fourth class, said fourth class including a plurality of concepts vertically linked with one another in hierarchical relationships, each of a plurality of said concepts of said third class being horizontally linked to each of a plurality of said concepts of said fourth class.

3. The apparatus of claim 2 wherein said class of diseases/diagnoses has one or more associated role relationships with one or more of the group of: (a) etiology, (b) morphology, (c) topography, (d) course, and (e) severity.

4. The apparatus of claim 3 wherein said class of topography has one or more associated role relationships with one or more of the group of: (a) part-of, (b) branch-of, and (c) tributary-of.

5. A method for retrieving electronic records from a database of medical records, comprising the steps of:

forming a knowledge base having a data structure set forth in a description language, said knowledge base including representations of a plurality of concepts within a plurality of classes, each of said classes comprising a nomenclature for medical terminology, each of said concepts in a first class being vertically linked to another of said concepts in said first class by a hierarchical relationship, each of said concepts in a second class being vertically linked to another of said concepts in said second class by a hierarchical relationship, each of said concepts in a third class being vertically linked to another of said concepts in said third class by a hierarchical relationship; said hierarchical relationships including parent relationships, child relationships, "is-a" relationships and "part-of" relationships; said nomenclature for said classes being selected from one or more of the group of: (a) diseases/diagnoses, (b) morphology, (c) living organisms, (d) physical agents, activities and forces, (e) chemicals, drugs, and biological products, (f) social context, (g) topography, (h) human bodily function, (i) treatment procedures, (j) etiology, k) spatial relationships, and (l) occupations;

a plurality of said concepts in said first class being horizontally linked to a plurality of said concepts in said second class by non-hierarchical relationships, a plurality of said concepts in said first class being horizontally linked to a plurality of said concepts in said third class by non-hierarchical relationships;

inputting a user query into a query manager and translating said query into a description language in said query manager;

accessing a database of encoded medical records; and analyzing said records in said database with a records analyzer based on said user query and said classes and said hierarchical and said non-hierarchical relationships in said knowledge base.

6. The method of claim 5 wherein each of a plurality of said concepts of said second class are horizontally linked to each of a plurality of said concepts of said third class, said knowledge base having a fourth class, said fourth class including a plurality of concepts vertically linked with one another in hierarchical relationships, each of a plurality of said concepts of said third class being horizontally linked to each of a plurality of concepts of said fourth class.

7. The method of claim 6 wherein said class of diseases/diagnoses has one or more associated role relationships from one or more of the group of: (a) etiology, (b) morphology, (c) topography, (d) course, and (e) severity.

8. The method of claim 7 wherein said class of topography has one or more associated role relationships with one or more of the group of: (a) part-of, (b) branch-of, and (c) tributary-of.

9. An apparatus for retrieving electronic records from a database of medical records, comprising:

a database of medical records, said medical records being encoded in a description language;

a knowledge base having a data structure set forth in said description language, said knowledge base including a plurality of classes having a plurality of concepts, each of said classes comprising a nomenclature for medical terminology, each of said concepts in a first class being vertically linked to another of said concepts in said first class by a hierarchical relationship, each of said concepts in a second class being vertically linked to another of said concepts in said second class by a hierarchical relationship, each of said concepts in a third class being vertically linked to another of said concepts in said third class by a hierarchical relationship;

said hierarchical relationships including parent relationships, child relationships, "is-a" relationships and "part-of" relationships;

said nomenclature for said classes including: (a) diseases/diagnoses, (b) morphology, (c) living organisms, (d) physical agents, activities and forces, (e) chemicals, drugs, and biological products, (f) social context, (g) topography, (h) human bodily function, (i) treatment procedures, (j) etiology, (k) spatial relationships, and (l) occupations;

a plurality of said concepts in said first class being horizontally linked to a plurality of said concepts in said second class by non-hierarchical relationships, a plurality of said concepts in said first class being horizontally linked to a plurality of said concepts in said third class by non-hierarchical relationships; each of said non-hierarchical relationships further comprises a role relationship;

a query manager that receives a user query and translates said query into a description language, said query seeking records from said database including classes or concepts identified in said query; and a records analyzer coupled to said query manager, said database and said knowledge base; said records analyzer analyzing said records in said database based on said user query and said non-hierarchical relationships in said knowledge base;

said records analyzer providing an identification of records in said database having coded representations corresponding to said user query from one or more of said classes and corresponding to each of said hierarchical relationships and each of said non-hierarchical relationships in said knowledge base, said identified records thereby including all of said records in said database having coded representations of concepts that are linked to the concepts specified in said user query by either hierarchical or non-hierarchical relationships.

10. The apparatus of claim 9 wherein said class of diseases/diagnoses has one or more associated non-hierarchical relationships with one or more of the group of: (a) etiology, (b) morphology, (c) topography, (d) course, and (e) severity.

11. The apparatus of claim 10 wherein said class of treatment procedure has one or more associated non-hierarchical relationships with one or more of the group of: (a) administered substance, (b) topography, (c) object of a procedure, and (d) equipment used to accomplish a procedure.

12. The apparatus of claim 11 wherein said class of treatment procedure has one or more associated non-hierarchical relationships with one or more laboratory test roles from the group of: (a) has-measured-component, said component being the substance or thing or physiological or physical function being measured, (b) has-method, said method being the method by which a procedure is performed, (c) has-property, said property being the kind of quantity being measured, (d) has-scale-type, said scale being the result of an observation of a diagnostic test, (e) has-specimen, said specimen being the bodily source, (f) has-subject-of-observation, said observation distinguishes observations or actions on the patient from observations or actions on non-patient materials that relate to the patient, and (g) has-time-aspect, said aspect being definitional temporal relationships for a procedure.

* * * * *